(12) United States Patent
Kumon

(10) Patent No.: US 6,391,307 B1
(45) Date of Patent: May 21, 2002

(54) COMPOSITION COMPRISING THE LOWER, NO-BRANCH CULM PORTION OF BAMBOO

(75) Inventor: Shigetomi Kumon, Saijo (JP)

(73) Assignee: Asahi Corporation, Ehime (JP)

( * ) Notice: Subject to any disclaimer, the term of this patent is extended or adjusted under 35 U.S.C. 154(b) by 0 days.

(21) Appl. No.: 09/158,513

(22) Filed: Sep. 22, 1998

(30) Foreign Application Priority Data

Nov. 12, 1997 (JP) ............................................. 9-326981

(51) Int. Cl.[7] ............................ A61K 35/78; A61K 9/14
(52) U.S. Cl. .................... 424/195.1; 424/489; 424/499; 514/777; 514/783; 530/500
(58) Field of Search ................. 514/777, 783; 424/195.1, 489; 530/500

(56) References Cited

U.S. PATENT DOCUMENTS 5,169,634 A * 12/1992 Ellingsen et al.
5,176,913 A * 1/1993 Homerlagen et al.
5,565,214 A * 10/1996 Zambo et al.

OTHER PUBLICATIONS

Aoyama J. Hokaido For. Prod. Res. Inst. 9:1–8 (1995) English Translation.*
Howarth J–Nutr. 126: 2519–2530 (1996) Abstract Only.*
Patent Abstracts of Japan, vol. 011, No. 379, Dec. 10, 1987 & JP 62–148425A (Mitsutoyo:KK; Others:01), Jul. 2, 1987.
Biological Abstracts, vol. 73, No. 8, 1982, Philadelphia, PA, U.S; Abstract No. 55480, Kuboyama, Noboru et al, "Anti-tumor Activities of Bamboo Leaf Extracts and Its Lignin" & Folia Pharmacol, JPN, vol. 77, No. 6, 1981, pp. 579–596.
S. Pravabati Devi et al, "Studies on the Nutritive Value and Anti–Carcinogenic Activities of Bamboo–Shoot Ferment on Mus–Musculus L.", J. Adv. Zool., vol. 10, No. 2, 1989, pp. 119–125.

* cited by examiner

Primary Examiner—Phillip Gambel
(74) Attorney, Agent, or Firm—Arent Fox Kintner Plotkin & Kahn

(57) ABSTRACT

An anticancer drug of which the main ingredient is bamboo powder. In particular, the bamboo powder is of lower no-branch culm portions of three-year-old and older bamboos, or is of bamboos cut down during the period of three months before the season of bamboo shoots; and pumpkin seed powder, garlic powder, powdered cheese, wheat flour, and water are added to the bamboo powder to make a mixture thereof, and the mixture is allowed to mature.

2 Claims, 1 Drawing Sheet

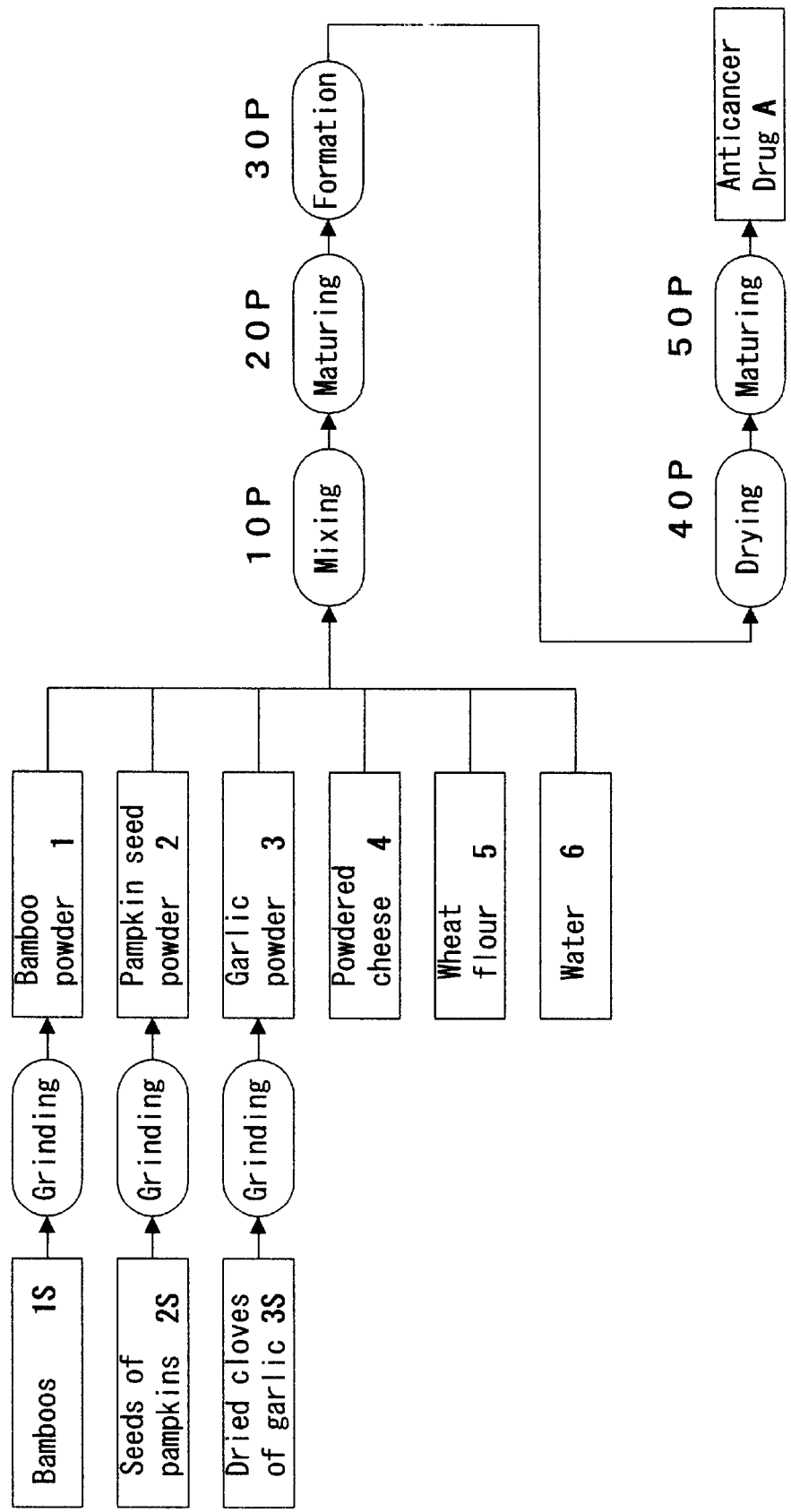

COMPOSITION COMPRISING THE LOWER, NO-BRANCH CULM PORTION OF BAMBOO

BACKGROUND OF THE INVENTION

The present invention relates to an anticancer drug effective in preventing colon and rectum cancer (cancer of the large intestine) of a high incidence, reducing the cholesterol value in plasma, and lowering the blood-sugar levels of diabetics.

Cancer has been taking a heavy toll of lives every year, and has recently become a representative of fatal diseases. On the other hand, research and development in medicines for, and treatments of, cancer are progressing rapidly. However, no fully effective medicine has been developed, and no fully effective treatment has been established. Accordingly, the prevention of cancer is most important.

One of the cancer-preventing measures is to remove such factors in our living environment as may cause cancer. Among such factors, food is the most fundamental factor. Food additives may contain cancer-inducing agents. Carcinogens may be produced while food is stored or cooked. It is known that the quality of food and nutrition have considerable relevance to the canceration.

For instance, vitamin A contained in vegetables is supposed to be effective for cancer prevention, and Vitamin C lowers the level of the production of nitrosamine in our bodies. Vegetable fiber improves bowel motions and reduces the incidence of colon and rectum cancer.(P.894, Vol. 3, Heibonsha's Encyclopedia)

It is important, therefore, to avoid foods which may be cancer-causing factors or contain carcinogens and to have foods which contain large quantities of vitamins and vegetable fiber.

As mentioned above, no fully effective medicine for cancer is available, and canceration processes have not completely been elucidated yet. Accordingly, it has not yet been elucidated which, in concrete terms, of such foods as containing large quantities of vitamins and fiber can prevent cancer effectively.

On the other hand, even if there is available a drug which prevents cancer quite effectively, it would tend to have side effects due to its very nature that it acts strongly on human bodies.

In accordance with the above, the object of the present invention is to provide an anticancer drug to reduce the incidence of colon and rectum cancer effectively without side effect.

SUMMARY OF THE INVENTION

According to the first aspect of the present invention, there is provided an anticancer drug of which the main ingredient is the powder of bamboos.

According to the second aspect of the present invention, there is provided an anticancer drug of which the main ingredient is the powder of the lower no-branch culm portions of three-year-old and older bamboos.

According to the third aspect of the present invention, there is provided an anticancer drug as claimed in claim 1 or 2 of which the bamboos are cut down during the period of three months before the season of bamboo shoots.

According to the third aspect of the present invention, there is provided an anticancer drug as claimed in claim 1 or 2 or 3 to which pumpkin seed powder, wheat flour, garlic powder, powdered cheese, and water are added to make a mixture thereof, which is allowed to mature.

The anticancer drug according to the first aspect of the invention reduces the incidence of colon and rectum cancer effectively without side effect.

The anticancer drug according to the second aspect of the invention contains large quantities of bamboo fiber, lignin, etc. and reduces the incidence of colon and rectum cancer effectively without side effect.

The anticancer drug according to the third aspect of the present invention contains large quantities of bamboo fiber, lignin, etc. and reduces the incidence of colon and rectum cancer effectively without side effect.

The anticancer drug according to the fourth aspect of the invention is formed into a shape suitable for taking it by mouth and reduces the incidence of colon and rectum cancer effectively without side effect.

BRIEF DESCRIPTION OF THE DRAWING

The features and advantages of the present invention will become more clearly appreciated from the following description in conjunction with the accompanying drawing, in which:

FIG. 1 is a flow sheet showing the process of one embodiment of anticancer drug of the present invention.

DETAILED DESCRIPTION OF THE PREFERRED EMBODIMENTS

With reference to the drawing, a preferred embodiment of the present invention will now be described.

In FIG. 1, the letter A represents an anticancer drug embodying the present invention. The ingredients of the anticancer drug A consists of a main ingredient of bamboos 1S and accessory ingredients. First, the main ingredient of bamboos 1S will be described. Any kinds of bamboos can be used as bamboos 1S, for any kinds of bamboos contain fiber, lignin, etc. For example, black bamboo (*Phyllostachys nigra*), common Japanese bamboo (*Phyllostachys bambusoides*), *mosochiku* (a species of thick-stemmed bamboo, or *Phyllostachys pubescens*), and so on can be used as bamboos 1S.

Any portions of a bamboo can be used as bamboos 1S, the main ingredient of the anticancer drug A. In particular, the lower no-branch culm portion of a three-year-old or older bamboo is suitable, for this portion contains more fiber, lignin, etc. than the other portion. Although we usually don't eat this portion of a bamboo, the inventor of the present invention dared to use this portion as the main ingredient. The effect of doing so will be described later.

Bamboos cut down in any seasons can be used as bamboos 1S, the main ingredient of the anticancer drug A. In particular, bamboos cut down during the period of three months before the season of bamboo shoots are most suitable as bamboos 1S, for bamboos accumulate nourishment in the period so that they can nourish bamboo shoots in their season. Therefore, bamboos cut down in the period contain more fiber, lignin, etc. than those cut down in the other period in a year. Its effect will be described later.

Bamboos 1S are reduced by a grinder to fine powder 1 of 0.1–20 micrometers or so.

The accessory ingredients of the anticancer drug A comprise the following materials.

Pumpkin seeds 2S are seeds taken from mature pumpkins and dried. These pumpkin seeds 2S are reduced by a grinder to fine powder 2 of 0.1–20 micrometers or so.

Dried cloves of garlic 3S are reduced by a grinder to fine powder 3 of 0.1–20 micrometers or so.

Powdered cheese 4 can be of any cheese without particular limitation.

Wheat flour 5 is to form the anticancer drug A into a granular, or bar-like, or some other shape, and any wheat flour without particular limitation can be used as wheat flour 5. Powder of glutinous rice may be used instead of wheat flour 5.

Any water without particular limitation can be used as water 6.

Moreover, all the accessory ingredients of pumpkin seed powder 2, garlic powder 3, powdered cheese 4, wheat flour 5, and water 6 can be dispensed with. However, as bamboo powder 1 alone is not suitable for taking it by mouth, it is preferable to add such accessory ingredients to the main one and mix them.

A process for preparing the anticancer drug A will now be described in sequence.

First, bamboo powder 1, pumpkin seed powder 2, garlic powder 3, powdered cheese 4, wheat flour 5, and water 6 are mixed in a mixing ratio described later (10P). The mixture is steamed for about two hours and allowed to mature for 48 hours at normal temperature (20P). Then, the compound is formed into a desired shape such as a granular, or bar-like, or any other shape (30P) Air of normal temperature is blown into the shaped pieces to dry them (40P), and they are further allowed to mature for 48 hours (50P) to become anticancer drug A of this embodiment.

The mixing weight ratio of the main ingredient of bamboo powder 1 and the accessory ingredients of pumpkin seed powder 2, garlic powder 3, powdered cheese 4, wheat flour 5, and water 6 will now be described.

Table 1 shows a mixing weight ratio of the main ingredient of bamboo powder 1 and the accessory ingredients of pumpkin seed powder 2, garlic powder 3, powdered cheese 4, wheat flour 5, and water 6. The higher the mixing weight ratio of the main ingredient of bamboo powder 1, the higher the medicinal effect of the anticancer drug A.

TABLE 1

| Mixing Weight Ratio | |
|---|---|
| Bamboo powder 1: | 80% |
| Pumpkin seed powder 2: | 5% |
| Garlic powder 3 | 5% |
| Powdered cheese 4 | 5% |
| Wheat flour 5 | 5% |
| Water 6: | Appropriate quantity |

To make it easy for us to take the anticancer drug A of this embodiment by mouth, it may be formed into tablets, grains, bars, and any other shapes. without particular limitation.

The medicinal effect of the anticancer drug A of this embodiment will now be described.

The appropriate quantity for an adult to take a day is about 25–50 g. This quantity is derived from experimental results described later and equivalent to 5–10% of the daily meal quantity of an ordinary adult. The quantity may be changed appropriately depending on each person's condition. It is appropriate to divide such a daily quantity into three to five doses.

The anticancer drug A of this embodiment improves the function of the digestive organs, which increases the quantity of excrement and prevents carcinogens from staying in the digestive organs. Thus, the anticancer drug A of this embodiment has a high effect in preventing cancer. Besides, the anticancer drug A of this embodiment has no side effects because its main ingredient, bamboos 1S, is natural bamboos.

Moreover, anticancer drug A prepared by using the lower no-branch culm portions of three-year-old and older bamboos as the main ingredient, bamboos 1S, has a higher effect, because three-year-old and older bamboos contain more fiber, lignin, etc. than younger bamboos do, and the lower no-branch culm portions contain more of the same than the upper branch-bearing culm portions do.

Furthermore, anticancer drug A prepared from bamboos cut down during the period of three months before the season of bamboo shoots has higher effect because the bamboos contain more fiber, lignin, etc. than bamboos cut down in the other months do.

Experiment

An experiment with the anticancer drug A of this embodiment will now be described.

To verify the medicinal effect of the fiber of the bamboos 1S to reduce the incidence of colon and rectum cancer to be induced by dimethylhydrazine (DMH), a carcinogen, an experiment was carried out as follows.

(1) Experimental Method

Male Wistar rats of about 80 g were fed with solid food on the market to acclimatize them to the feeding environment. Then, they were divided into. four groups, each consisting of 15. The four groups were fed with different diets shown below and observed for 20 weeks.

In the first 10 weeks, 0.03 g/kg DMH dissolved in corn oil was administered to the rats in Groups 2, 3, and 4 through a stomach tube every week. In the eleventh week, the moving speed of food through the digestive tract (from mouth to anus) and the quantity of excrement of each rat were measured. In the twentieth week, they were anesthetized with ether and their large intestines were removed. The large intestines were washed with cold physiological saline to examine them for cancer cells.

TABLE 2

| Experimental Feed (g/kg) | | | | |
|---|---|---|---|---|
| | Group 1 | Group 2 | Group 3 | Group 4 |
| DMH | — | 0.03 | 0.03 | 0.03 |
| Bamboo fiber | — | — | 50 | 100 |
| Casein | 200 | 200 | 200 | 200 |
| Corn oil | 50 | 50 | 50 | 50 |
| Minerals | 40 | 40 | 40 | 40 |
| Vitamins | 10 | 10 | 10 | 10 |
| Sucrose | 700 | 700 | 650 | 600 |

The bamboos 1S were mosochiku (a species of thick-stemmed bamboo or *Phyllostachys pubescens*). The fiber of the bamboos 1S contained 56% cellulose and 24% lignin. Table 3 shows the constituent parts contained in 100 g of the bamboo 1S.

TABLE 3

| Constituent Parts in 100 g of Mosochiku | |
|---|---|
| Constituent Parts | Quantity |
| Water | 4.98 g |
| Protein | 1.13 g |
| Lipid | 0.22 g |
| Sugar | 48.23 g |
| Fiber | 44.39 g |
| Ash | 1.05 g |
| Calcium | 28.00 mg |

TABLE 3-continued

Constituent Parts in 100 g of Mosochiku

| Constituent Parts | Quantity |
|---|---|
| Iron | 5.40 mg |
| Phosphorus | 34.00 mg |
| Tyrosine | 0.40 mg |

(2) Experimental Results

Table 4 shows the experimental results.

TABLE 4

Experimental Results

| Moving Speed of Food through Digestive Tract (hours) | Quantity of Excrement (wet weight, g/24 hrs./rat) | Incidence of Colon and Rectum Cancer (%) |
|---|---|---|
| Group 1 16.9 ± 1.5 | 0.6 ± 0.2 | 0 (0/15) |
| Group 2 17.2 ± 1.2 | 0.6 ± 0.3 | 100 (15/15) |
| Group 3 12.5 ± 0.9 | 2.5 ± 0.3 | 60 (9/15) |
| Group 4 10.2 ± 0.6 | 3.2 ± 0.4 | 47 (7/15) |

DMH was not administered to the rats of Group 1. Accordingly, their incident of DMH-induced cancer was 0%.

DMH was administered to the rats of Group 2, but no fiber of the bamboos 1S was fed to them. Their incident of DMH-induced cancer was 100%.

DMH was administered and the fiber of the bamboos 1S was fed to the rats of Groups 3 and 4. As the result of it, the incidences of DMH-induced cancer of Groups 3 and 4 were reduced to 60% and 47%., respectively, demonstrating the effect of the fiber of the bamboos 1S.

Besides, the rats of Group 4 were fed with two times the quantity of bamboo fiber fed to those of Group 3. Thus, it was demonstrated that the fiber contained in the bamboos 1S reduces the incident of DMH-induced colon and rectum cancer.

The fiber contained in the bamboos 1S increased the moving speed of food in the digestive tract and the quantity of excrement. The increased excrement can be considered to have reduced the incidence of DMH-induced colon and rectum cancer. Namely, the fiber contained in the bamboos 1S clearly reduced the incident of DMH-induced colon and rectum cancer.

As shown in Table 4, the fiber contained in the bamboos 1S increased the quantity of excrement and reduced the necessary time for food to pass through the large intestine in particular. As the result of it, the dimethylhydrazine (DMH) was diluted to such an concentration as did not cause cancer and, at the same time, its acting time in the large intestine was reduced, which resulted in the reduced incidences of DMH-induced colon and rectum cancer.

On the other hand, lignin is known to activate the immune system. The fiber of the bamboos 1S contained a large quantity of lignin, which can be considered to have contributed to the reduction of incidence of colon and rectum cancer.

In these days, some people are suffering from anorexia, worrying too much about obesity with food around which tends to be rich in fat and protein. The inventor of the present invention has successfully reduced his weight from 66.5 kg to 62.5 kg by having ordinary meals and taking a quantity of fiber of the bamboos 1S equivalent to 5% of his daily meal quantity for 60 days.

The inventor of the present invention has been suffering from diabetes. His blood-sugar level used to be 220–250 two hours after having a meal. It has been reduced to 160–180 by having a quantity of fiber of the bamboos 1S equivalent to 5% of daily meal quantity for 60 days. In addition, his skin trouble from athlete's foot over a long time period changed from wet type to dry type and has completely been cured.

The fiber of the bamboos 1S demonstrated its effect to prevent obesity, decrease the cholesterol value in plasma, prevent colon and rectum cancer, and also help the treatment of skin troubles.

I claim:

1. A pharmaceutical composition suitable for use as an anticancer drug, consisting of an anticancer effective amount of bamboo powder, pumpkin seed powder, wheat flour, garlic powder, powdered cheese and water in combination with a pharmaceutically acceptable carrier or diluent, wherein the bamboo powder is produced by the following process:

providing, as a starting material, a lower no-branch culm portion of at least three-year-old bamboo; and converting the starting material into a powder.

2. A pharmaceutical composition suitable for use as an anticancer drug, consisting of bamboo powder, pumpkin seed powder, wheat flour, garlic powder, powdered cheese and water in combination with a pharmaceutically acceptable carrier or diluent, wherein the bamboo powder is produced by the following process:

providing, as a starting material, a lower no-branch culm portion of at least three-year-old bamboo; and grinding the starting material to a powder.

* * * * *